US010393703B2

(12) United States Patent
Fouda et al.

(10) Patent No.: US 10,393,703 B2
(45) Date of Patent: Aug. 27, 2019

(54) MULTI-POINT IN SITU CALIBRATION OF ELECTROMAGNETIC PIPE INSPECTION TOOLS

(71) Applicant: HALLIBURTON ENERGY SERVICES, INC., Houston, TX (US)

(72) Inventors: Ahmed E. Fouda, Houston, TX (US); Burkay Donderici, Houston, TX (US); Luis Emilio San Martin, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/531,369

(22) PCT Filed: Aug. 12, 2016

(86) PCT No.: PCT/US2016/046864
§ 371 (c)(1),
(2) Date: May 26, 2017

(87) PCT Pub. No.: WO2018/031047
PCT Pub. Date: Feb. 15, 2018

(65) Prior Publication Data
US 2018/0106764 A1 Apr. 19, 2018

(51) Int. Cl.
*G01N 27/90* (2006.01)
*G01V 3/38* (2006.01)
(Continued)

(52) U.S. Cl.
CPC ......... *G01N 27/9086* (2013.01); *E21B 47/00* (2013.01); *G01N 17/04* (2013.01);
(Continued)

(58) Field of Classification Search
CPC .. G01N 27/9086; G01N 17/04; G01N 27/902; G01V 3/10; G01V 3/38; G01V 13/00; E21B 47/00
(Continued)

(56) References Cited

U.S. PATENT DOCUMENTS 4,292,589 A    9/1981   Bonner et al.
6,636,045 B2 * 10/2003   Tabarovsky ............. G01V 3/28
                                                 324/343

(Continued)

FOREIGN PATENT DOCUMENTS

WO    2015/157268    10/2015

OTHER PUBLICATIONS

PCT International Search Report and Written Opinion, dated May 10, 2017, Appl No. PCT/US2016/046864, "Multi-Point in Situ Calibration of Electromagnetic Pipe Inspection Tools," Filed Aug. 12, 2016.
(Continued)

*Primary Examiner* — Reena Aurora
(74) *Attorney, Agent, or Firm* — Benjamin Fite; C. Tumey Law Group PLLC

(57) ABSTRACT

A calibration system for an electromagnetic (EM) tool includes a processor. The processor employs the EM tool to measure responses at each of a plurality of channels. The processor records the measured responses at each of the channels in an EM data log for the channel. The processor determines a nominal value of each of the channels, as being equal to a histogram peak of the EM data log. The processor selects one or more calibration points from the EM data log for a particular channel, based on a difference between the nominal value of the particular channel and the measured response at the calibration point being greater than a particular threshold. The processor determines a plurality of
(Continued)

parameters by reducing a misfit between synthetic data and both the nominal values of the channels and the measured responses of the channels at the selected one or more calibration points.

20 Claims, 7 Drawing Sheets

(51) Int. Cl.
    *E21B 47/00* (2012.01)
    *G01V 13/00* (2006.01)
    *G01N 17/04* (2006.01)
    *G01V 3/10* (2006.01)
    *G01V 3/28* (2006.01)

(52) U.S. Cl.
    CPC ............ *G01N 27/902* (2013.01); *G01V 3/10* (2013.01); *G01V 3/28* (2013.01); *G01V 3/38* (2013.01); *G01V 13/00* (2013.01)

(58) Field of Classification Search
    USPC ........................................ 324/338, 339, 202
    See application file for complete search history.

(56) References Cited

U.S. PATENT DOCUMENTS

| 2009/0195244 A1 | 8/2009 | Mouget et al. |
|---|---|---|
| 2010/0134112 A1 | 6/2010 | Zhang et al. |
| 2010/0263449 A1 | 10/2010 | Bolshakov et al. |
| 2015/0338541 A1 | 11/2015 | Nichols et al. |
| 2016/0245952 A1* | 8/2016 | Dupuis .................... G01V 3/18 |

OTHER PUBLICATIONS

PCT International Search Report and Written Opinion, dated May 12, 2017, Appl No. PCT/US2016/046858, "Tool and Method to Make High Resolution and High Penetration Measurement of Corrosion," Filed Aug. 12, 2016.

PCT International Search Report and Written Opinion, dated May 12, 2017, Appl No. PCT/US2016/046857, "Method for in-Situ Calibration of Electromagnetic Corrosion Detection Tools," Filed Aug. 12, 2016.

ACUNA, Irlec Alexandra et al., "Scanning for downhole corrosion," Oilfield Review, Spring 2010, pp. 42-50, vol. 22, No. 1, Schlumberger.

Rourke, Marvin et al., "Multi-tubular corrosion inspection using a pulsed eddy current," IPTC 16645, Mar. 26-28, 2013, Beijing, China.

PCT/US2016/046857; filed Aug. 12, 2016, Ahmed E. Fouda, Method for in-Situ Calibration of Electromagnetic Corrosion Detection Tools.

PCT/US2016/046858; filed Aug. 12, 2016, Reza Khalaj Amineh, Tool and Method to Make High Resolution and High Penetration Measurement of Corrosion.

* cited by examiner

MULTI-POINT IN SITU CALIBRATION OF ELECTROMAGNETIC PIPE INSPECTION TOOLS

BACKGROUND

For oil and gas exploration and production, a network of well installations and other conduits are established by connecting sections of metal tubing together. For example, a well installation may be completed, in part, by lowering multiple sections of metal tubing (e.g., a casing string) into a borehole, and cementing the metal tubing in place. In some well installations, multiple tubing strings are employed (e.g., a concentric multi-string arrangement) to allow for different operations related to well completion, production, or enhanced oil recovery (EOR) options.

Corrosion of metal tubing is an ongoing issue. Efforts to mitigate corrosion include use of corrosion-resistant alloys, coatings, treatments, corrosion transfer, etc. Also, efforts to improve corrosion monitoring are ongoing. For downhole tubing strings, various types of corrosion monitoring tools are available. One type of corrosion detection tool uses electromagnetic (EM) fields to estimate tubing wall thickness or other corrosion indicators. As an example, an EM logging tool may collect EM log data, where the EM log data can be interpreted to correlate a level of flux leakage or EM induction with corrosion. When multiple tubing strings are employed together, correctly managing corrosion detection EM logging tool operations and data interpretation is not a trivial task.

BRIEF DESCRIPTION OF THE DRAWINGS

Accordingly, there are disclosed in the drawings and the following description a systems and related methods for calibrating an electromagnetic (EM) logging tool (e.g., EM pipe inspection tool). In the drawings.

Figure 1A:
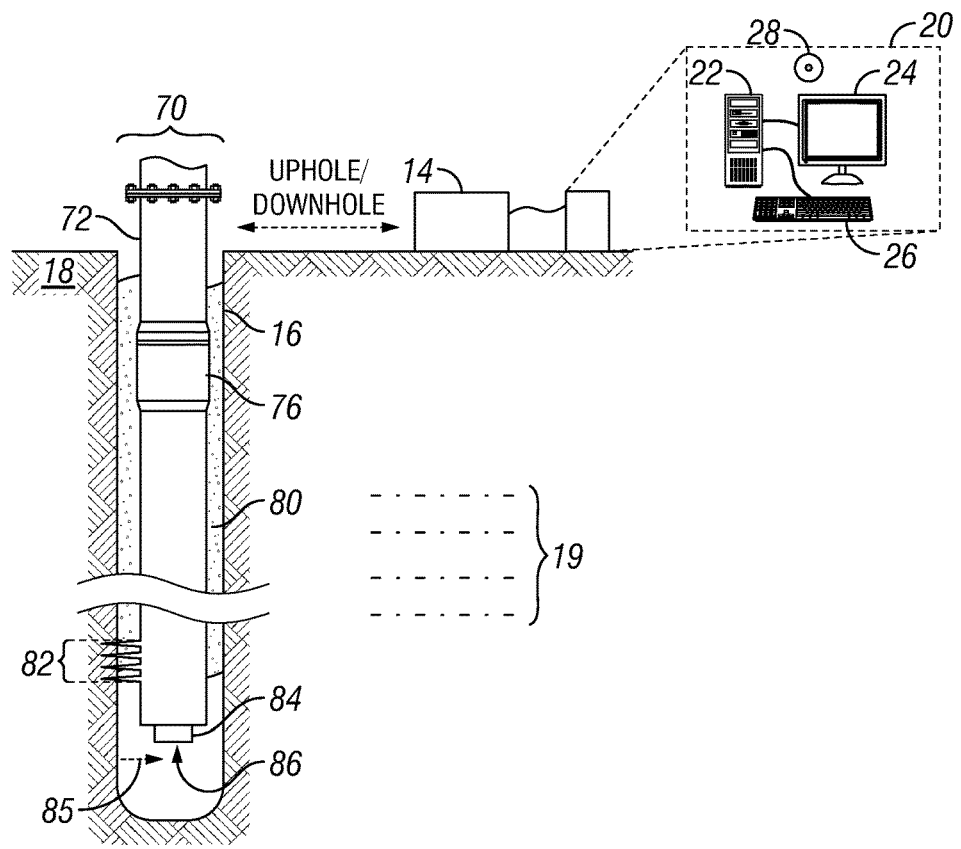
FIGS. 1A and 1B depict an illustrative multi-string corrosion survey environment.

It should be understood, however, that the specific embodiments given in the drawings and detailed description do not limit the disclosure. On the contrary, they provide the foundation for one of ordinary skill to discern the alternative forms, equivalents, and modifications that are encompassed together with one or more of the given embodiments in the scope of the appended claims.

DETAILED DESCRIPTION

Disclosed herein are systems and related methods for calibrating an electromagnetic (EM) logging tool (e.g., EM pipe inspection tool). To distinguish between different tubing strings in a multi-string scenario, the EM logging tool may employ different components and/or different operations for each tubing string. For example, the EM logging tool may include different sensor arrays to enable collection of EM log data that corresponds to different tubing strings. Once EM log data corresponding to different tubing strings is collected, it is processed. The processing of EM log data may be performed downhole and/or at earth's surface to derive attributes (e.g., tubing diameter, tubing wall thickness, conductivity, and/or permeability) for each of multiple tubing strings as a function of depth. The derived attributes can further be correlated with one or more types of corrosion and/or with a corrosion index. If corrosion of a particular tubing string is determined to exceed a threshold, a corrective action may be performed. Example corrective actions include enhancing, repairing, or replacing at least part of a tubing segment. Additionally or alternatively, a treatment can be applied to reduce the rate of corrosion for at least part of a tubing segment.

Particular embodiments relate to calibrating an EM logging tool. In at least some embodiments, a method includes disposing the EM tool in a plurality of tubing strings, and employing the EM tool to measure responses at each of a plurality of channels, wherein each of the channels is defined by a corresponding receiver coil of the plurality of receiver coils and a corresponding frequency of a plurality of frequencies. The method further includes recording the measured responses at each of the plurality of channels in an EM data log for the channel, and determining a nominal value over a section of the log of each of the plurality of channels, as being equal to a histogram peak of the EM data log for the channel. The method further includes selecting one or more calibration points from the EM data log for a particular channel of the plurality of channels, based on a difference (e.g., absolute difference) between the nominal value of the particular channel and the measured response at the calibration point being greater than a particular threshold in a given depth range. The method further includes determining a plurality of parameters by reducing a misfit between synthetic data and both the nominal values of the plurality of channels and the measured responses of the plurality of channels at the selected one or more calibration points. The plurality of parameters includes at least a nominal magnetic permeability of each of the tubing strings, a nominal electrical conductivity of each of the tubing strings, a diameter of each of the tubing strings at each of the selected one or more calibration points, a thickness of each of the tubing strings at each of the selected one or more calibration points, a magnetic permeability of each of the tubing strings at each of the selected one or more calibration points, an electrical conductivity of each of the tubing strings at each of the selected one or more calibration points, or a set of calibration coefficients for each of the channels. The set of calibration coefficients for each of the channel s includes an additive coefficient and at least one multiplicative coefficient.

A related system includes a processor. The processor employs the EM tool to measure responses at each of a plurality of channels. Each of the channels is defined by a corresponding receiver coil of the plurality of receiver coils and a corresponding frequency of a plurality of frequencies. The processor records the measured responses at each of the plurality of channels in an EM data log for the channel. The processor determines a nominal value of each of the plurality of channels, as being equal to a histogram peak of the EM data log for the channel. The processor selects one or more calibration points from the EM data log for a particular channel of the plurality of channels, based on a difference (e.g., absolute difference) between the nominal value of the particular channel and the measured response at the calibration point being greater than a particular threshold in a given depth range. The processor determines a plurality of parameters by reducing a misfit between synthetic data and both the nominal values of the plurality of channels and the measured responses of the plurality of channels at the selected one or more calibration points. The plurality of parameters includes at least a nominal magnetic permeability of each of the tubing strings, a nominal electrical conductivity of each of the tubing strings, a diameter of each of the tubing strings at each of the selected one or more calibration points, a thickness of each of the tubing strings at each of the selected one or more calibration points, a magnetic permeability of each of the tubing strings at each of the selected one or more calibration points, an electrical conductivity of each of the tubing strings at each of the selected one or more calibration points, or a set of calibration coefficients for each of the channels. The set of calibration coefficients for each of the channels includes an additive coefficient and at least one multiplicative coefficient.

Figure 1B:
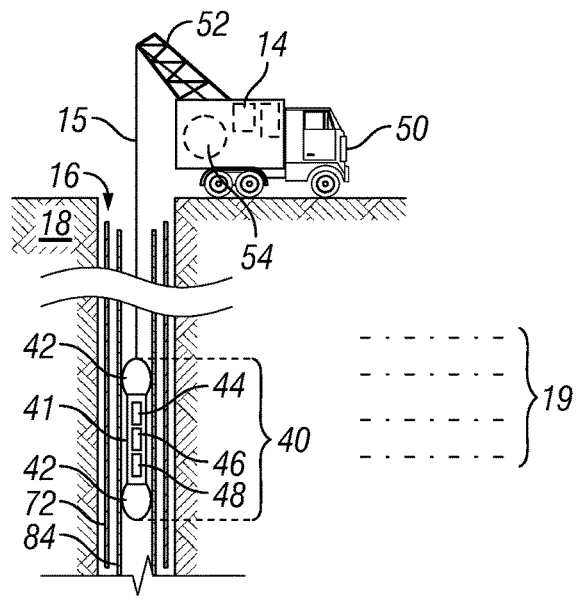

To provide some context for the disclosure, FIGS. 1A and 1B show an illustrative multi-string corrosion survey/monitoring environment. FIG. 1A shows a borehole 16 that penetrates formations 19 of the earth 18. A casing string 72 is positioned in the borehole 16 and secured in place by a cement sheath 80. Further, a production tubing string 84 has been positioned in an inner bore of the casing string 72.

The casing string 72 and production tubing 84 of well 70 are formed from multiple tubular sections (usually about 30-40 feet long) connected end-to-end by couplings 76. It should be noted that FIG. 1A is not to scale, and that each tubing string typically includes many such couplings 76. Both the casing string 72 and the production tubing string 84 are typically formed of metal pipe and are subject to corrosion.

The production tubing string 84 defines both central and annular flow paths for fluids. With reference to FIG. 1A, the well 70 corresponds to a production well and the production tubing string is adapted to guide a desired fluid (e.g., oil or gas) from a bottom of the borehole 16 to a surface of the earth 18. Accordingly, perforations 82 may be formed in the casing string 72 or at a bottom of the borehole 16 to facilitate the flow of a fluid 85 from a surrounding formation into the borehole 16 and thence to earth's surface via the central flow path which can be accessed via an opening 86 at the bottom of the production tubing string 84. Note that well configuration of FIG. 1A is illustrative and not limiting on the scope of the disclosure. Other examples of permanent well installations include injection wells and monitoring wells. Further, well 70 may include additional casing or tubing strings to provide additional flow paths to the surface, e.g., from multiple production zones.

FIG. 1A further illustrates a surface interface 14 and/or computer system 20 for collecting data from downhole sensors and perhaps controlling downhole actuators to optimize production. In some embodiments, the surface interface 14 and/or the computer system 20 may be supplied with EM log data collected by an EM logging tool and tasked with processing the EM log data to determine and monitor tubing string attributes as described herein. In at least some embodiments, the computer system 20 includes a processor 22 that performs the EM log data analysis operations by executing software or instructions obtained from a local or remote non-transitory computer-readable medium 28. The processor 22 may be, for example, a general purpose microprocessor, a microcontroller, a digital signal processor, an application specific integrated circuit, a field programmable gate array, a programmable logic device, a controller, a state machine, gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium. The computer system 20 also may include input device(s) 26 (e.g., a keyboard, mouse, touchpad, etc.) and output device(s) 24 (e.g., a monitor, printer, etc.). Such input device(s) 26 and/or output device(s) 24 provide a user interface that enables an operator to interact with an EM logging tool and/or software executed by the processor 22. For example, the computer system 20 may enable an operator to select analysis options, view collected EM log data, view analysis results, and/or perform other tasks.

The EM logging tool can take various forms, including that of the wireline tool 40 illustrated in FIG. 1B. EM logging tool 40 is positioned within production tubing string 84 and casing string 72, suspended by a cable 15 having conductors and/or optical fibers for conveying power to the EM logging tool 40. The cable 15 may also be used as a communication interface for uphole and/or downhole communications. The cable 15 wraps and unwraps as needed around cable reel 54 when lowering or raising the EM logging tool 40. As shown, the cable reel 54 may be part of a movable logging facility or vehicle 50 having a cable guide 52.

The EM logging tool 40 may include stabilizers 42 on one or more ends (e.g. opposite ends) of main body 41 to centralize the tool 40 within the innermost production tubing string 84. The main body 41 of the EM logging tool 40 includes control electronics 44, transmitter(s) 46, and receiver(s) 48. In operation, transmitter(s) 46 are directed by the control electronics 44 to generate a time-varying EM field whose magnetic flux is guided and modified by the production tubing string 84 and/or tubing string 72. The magnetic flux induces a voltage in receiver(s) 48. The magnetic flux modification provided by the production tubing string 84 and/or tubing string 72 is lossy due to induced eddy currents. The control electronics 44 store the voltages recorded by receiver(s) 48 as a function of tool position to form an EM data log, which may be correlated with geometrical, electrical, and/or magnetic attributes of the production tubing string 84 and/or tubing string 72. Corrosion of the production tubing string 84 and/or tubing string 72 affects their geometrical, electrical, and/or magnetic attributes and can therefore be estimated from analysis of the EM log data. The control electronics 44 may also include a communication interface to transmit the EM data log to earth's surface. Additionally or alternatively, the EM data log obtained by the EM logging tool 40 can be stored and accessed later once the tool 40 reaches earth's surface.

In FIG. 1B, the surface interface 14 receives the EM data log via the cable 15 and conveys the EM field measurements to a computer system 20. Again, the interface 14 and/or computer system 20 (e.g., part of the movable logging facility or vehicle 50) may perform various operations such as converting signals from one format to another, storing the EM log data, and/or analyzing the EM log data to determine tubing string attributes.

Figure 2A:
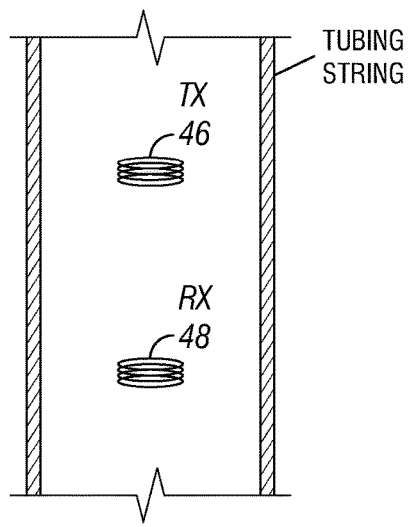
FIGS. 2A and 2B show illustrative transmitter/receiver configurations for an EM logging tool for multi-string corrosion monitoring.
Figure 2B:
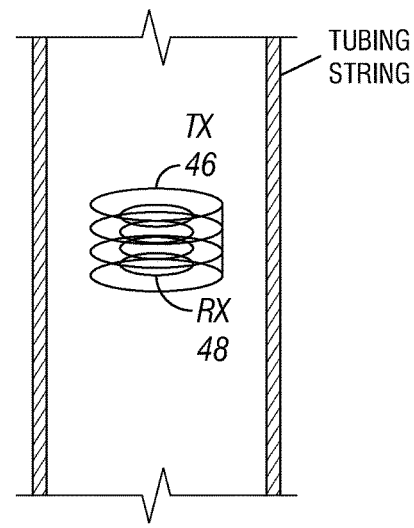

FIGS. 2A and 2B show illustrative transmitter/receiver configurations suitable for an EM logging tool (e.g., tool 40). With reference to FIG. 2A, transmitter 46 and receiver 48 are coaxially positioned within a tubing string (e.g., strings 72 and/or 84) and are separated along the tool axis. With reference to FIG. 2B, transmitter 46 and receiver 48 are coaxially positioned within a tubing string (e.g., strings 72 and/or 84) and are collocated. For example, transmitter 46 and receiver 48 may correspond to coils or solenoids, where the receiver 48 is positioned inside the transmitter 46, or vice versa. While only one transmitter 46 and one receiver 48 are illustrated in FIGS. 2A and 2B, it should be understood that EM logging tools such as tool 40 may have a plurality of sensor arrays, where the distance between transmitters 46 and receivers 48 for different sensor arrays may vary. For example, multiple receivers may provide measurements in response to the operation of a given transmitter; conversely, a given receiver may provide measurements in response to the operation of multiple transmitters. Further, the dimensions of the transmitters 46 and receivers 48 may vary for different sensor arrays. Where multiple transmitters are employed, their operation may be frequency multiplexed and/or time multiplexed. In some embodiments, a given transmitter may transmit a multi-frequency signal or a broadband signal. Different frequencies may be chosen to correspond to different tubing diameters. Similarly, where transmit pulses are used, different time delays may correspond to different tubing diameters.

Figure 3:
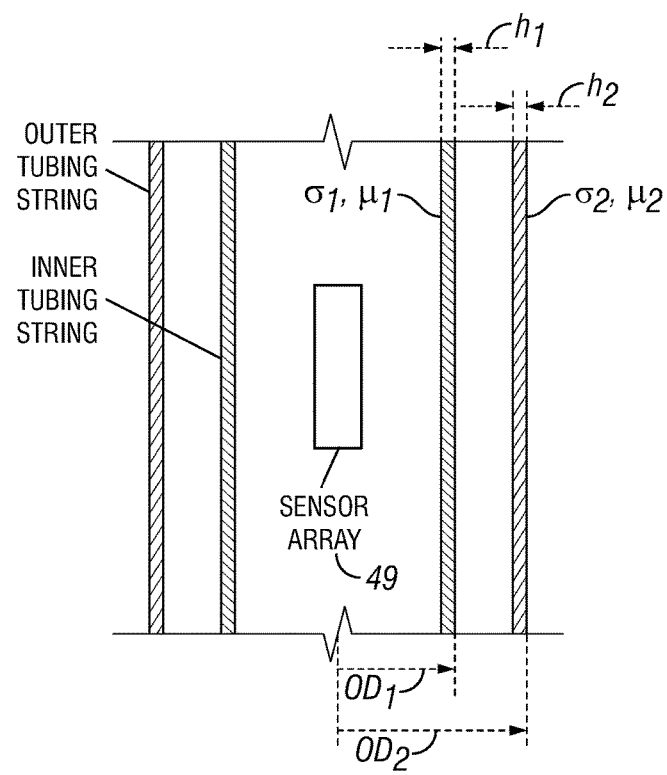
FIG. 3 shows illustrative attributes of a multi-string model.

FIG. 3 shows illustrative attributes of a multi-string model. With reference to FIG. 3, a sensor array 49 (e.g., one or more transmitter/receiver arrays) is positioned within two tubing strings (inner and outer tubing strings). The sensing array 49 may be part of an EM logging tool such as tool 40 to enable various attributes of the inner and outer tubing strings to be estimated. In the illustrative survey environment of FIGS. 1A and 1B, the tubing string 72 is an outer (casing) string, while the production tubing string 84 is an inner (production tubing) string.

One-dimensional (1D) forward and inversion models may be used to calculate multi-string tubing wall thickness/corrosion attributes. For the two-string tubing model of FIG. 3, tubing wall thickness parameters are assumed to be uniform along the axial direction. If tubing materials are known, the attributes to be determined for the inner tubing string may include outer diameter ($OD_1$), tubing wall thickness ($h_1$), conductivity ($\sigma_1$), and/or magnetic permeability ($\mu_1$). Similarly, the attributes to be determined for the outer tubing string may include outer diameter ($OD_2$), tubing wall thickness ($h_2$), conductivity ($\sigma_2$), and/or magnetic permeability ($\mu_2$).

To calculate the tubing wall thickness, a numerical optimization (e.g., a Gauss-Newton method) may be employed. In such case, unknown parameters are adjusted until the misfit error between measurement data and predicted data (computed via forward modeling using estimated parameters) is sufficiently small. This goal can be achieved by iteratively solving a non-linear problem that minimizes the objective cost function:

$$C(X) = \frac{1}{2}[\|e(X)\|^2], \quad (1)$$

where the residual factor is defined as:

$$e(X) = \begin{bmatrix} S_1(X) - m_1 \\ S_2(X) - m_2 \\ \vdots \\ S_j(X) - m_j \\ \vdots \\ S_M(X) - m_M \end{bmatrix}, \quad (2)$$

where $S_j(X)$ is the modeled tool response corresponding to a particular value of tubing attribute vector X. For a single tubing string scenario, $X = [OD; h; \sigma; \mu]$. If tubing OD and tubing material are known or predetermined, X is simply equal to tubing thickness h, $m_j$ is the corresponding measured data, and $\|.\|^2$ refers to the L2-norm. If the EM logging tool 40 is operated as a time-domain tool, measured data $m_j$ are usually selected time bins that may correspond to different sets of tubing string diameters. On the other hand, if the EM logging tool 40 is operated at a frequency or multiple frequencies, measured data $m_j$ are collected signals at the frequency or frequencies used. If multiple sensor arrays are employed in the EM logging tool 40, measured data $m_j$ are tool responses (frequency or time-domain) from all of the selected arrays.

The scheme described with reference to Equations (1) and (2) can be implemented straightforwardly by using classical optimization methods. However, it becomes inefficient when the optimization problem is relatively large such as when dealing with a multi-string scenario. Mathematically, as more unknowns are introduced into the inversion model, the final results become more unstable.

Observed from simulation results and theory of EM wave propagation, shorter sensor arrays with higher frequency (or with an earlier time channel) are more sensitive to an inner tubing string (e.g., production tubing string 84). On the other hand, longer sensor arrays with lower frequency (or with a later time channel) are sensitive to both inner and outer strings (e.g., both production tubing string 84 and tubing string 72). These behaviors enable calculation of inner string attributes using a simplified inversion model without taking the outer string into account. After estimating the inner string attributes, the outer string attributes can be computed afterwards in different ways.

According to at least one embodiment, an EM pipe inspection tool (e.g., an EM corrosion detection tool, an EM logging tool 40) is calibrated while the tool is run inside two or more well tubing strings (e.g., outer string, inner string of FIG. 3). Running corrosion detection tools in the production tubing may be performed as part of downhole corrosion detection. Early detection of corrosion in well tubing strings promotes the integrity and the safety of the well.

Different types of corrosion detection tools include mechanical calipers, ultrasonic acoustic tools, cameras, EM flux leakage, and EM induction tools. Among these tools, EM induction tools can be used to detect corrosion in outer casings (e.g., outer string of FIG. 3) beyond one or more inner strings in which the tool is run.

An EM induction tool includes at least one transmitter (e.g., transmitting coil) and at least one receiver (e.g., receiving coil). The transmitter induces eddy currents inside the metallic pipes (e.g., well casings, or casing strings), and the receiver records secondary fields generated from the pipes. Those secondary fields bear information about the electrical properties and metal content of the pipes and can be inverted for any corrosion or loss in metal content of the pipes.

Figure 4:
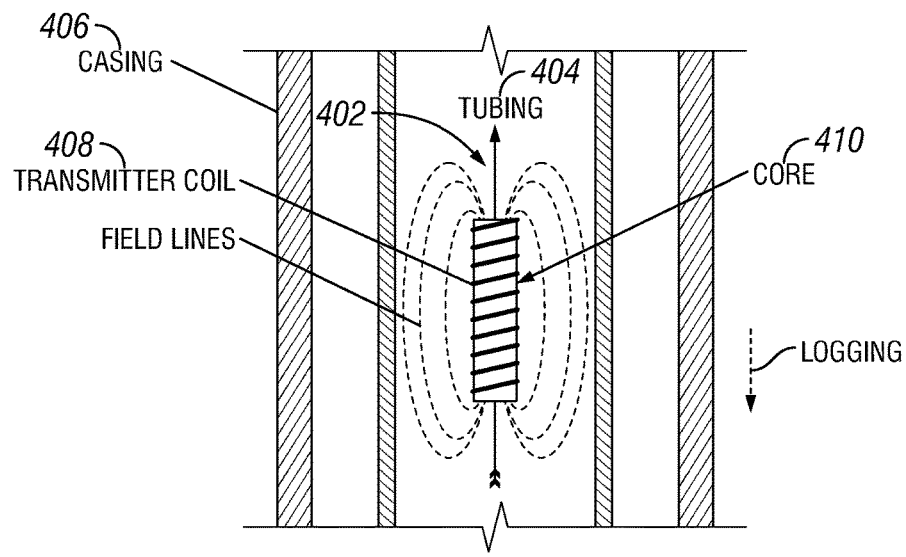
FIG. 4 depicts an illustrative logging scenario.

FIG. 4 depicts an illustrative logging scenario. With reference to FIG. 4, a corrosion detection tool transmitter 402 is run inside a tubing 404 (e.g., production tubing string 84) and a casing 406 (e.g., casing string 72). The tool transmitter 402 includes a coil 408 that is wrapped around a core 410. Usually, cores are made of high permeability materials, the relative permeability of which can range from 50-300 or more when constructed of a single piece of high magnetic permeability material.

Figure 5:
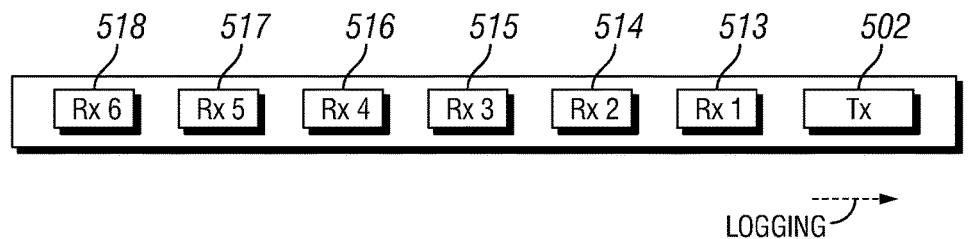
FIG. 5 illustrates an example of an axial arrangement of receivers of a corrosion detection tool.

FIG. 5 illustrates an example of an axial arrangement of receivers of a corrosion detection tool. The tool includes a transmitter 502 and receivers 513, 514, 515, 516, 517, 518. The receivers 513, 514, 515, 516, 517, 518 are positioned at respective distances (or axial spacings) away from the transmitter 502, with respect to a direction of logging.

EM induction tools can be frequency-domain tools that operate at discrete set of frequencies (e.g., higher frequencies to inspect inner pipes and lower frequencies to inspect outer pipes). Alternatively, EM induction tools can operate in the time domain by transmitting transient pulses and measuring the decay response versus time (e.g., earlier time(s) corresponds to inner pipes and later time(s) corresponds to outer pipes). Such tools are referred to as pulsed eddy current corrosion detection tools.

The way(s) in which a core (e.g., core 410) affects measurements (e.g., measurements made at a receiver) depends on various factors, e.g., environmental factors such as the number of pipes inside which the tool is run, the thicknesses of the walls of the pipes, the diameters of the pipes, and electromagnetic properties (conductivity and permeability) of the pipes. Therefore, tool calibration is preferably performed in situ while the tool is run inside the well.

For a given well, various characteristics of the pipes (e.g., the number of pipes, the outer diameters of the pipes, the nominal thickness of each pipe) may be known a priori. However, the magnetic permeability and electrical conductivity of each pipe may not be known precisely. Also, the values of these parameters may vary substantially from one casing section to another. Therefore, calibration is performed to account for effects of the core, as well as to determine estimates of the magnetic permeability and the electrical conductivity of the pipes within each casing section.

As noted earlier, EM corrosion detection tools may be of different types (frequency domain tools, time domain tools). Regardless of the type of the EM corrosion detection tool, measurements made at different receivers and different channels (e.g., frequencies in the case of frequency-domain tools, or time slots in the decay response in case of time-domain tools) are preferably calibrated before the measurements are compared with simulated results as part of the processing to estimate pipe wall thickness.

Figure 6:
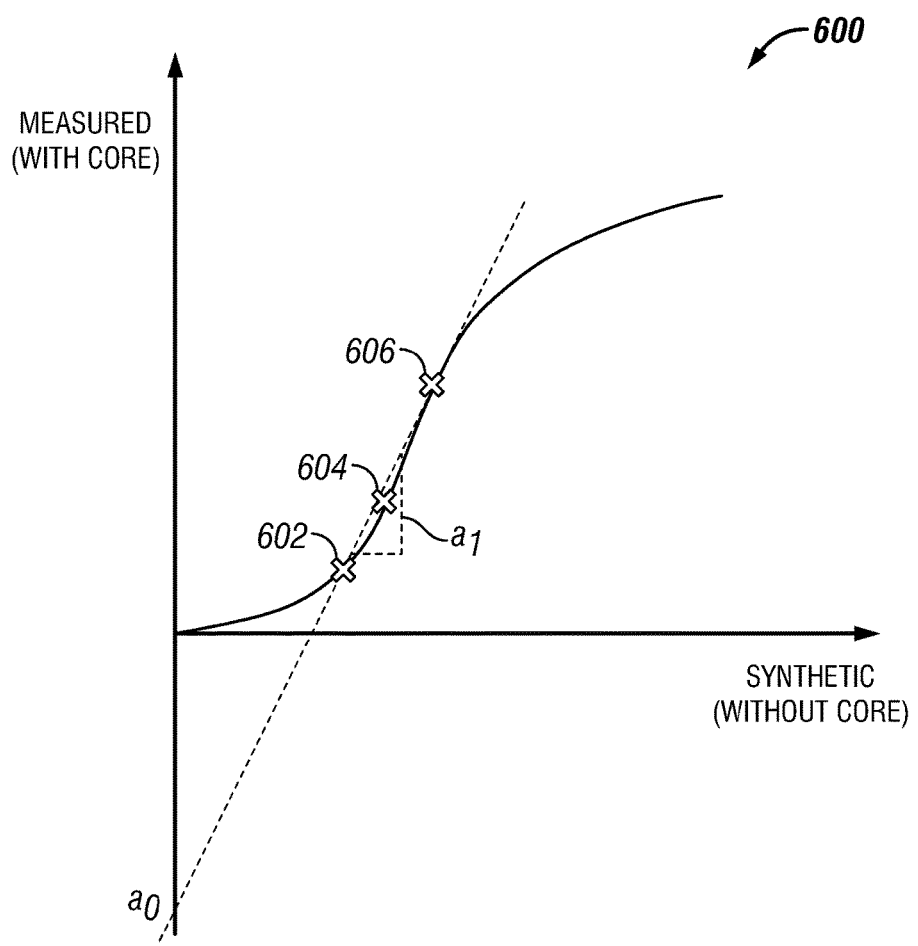
FIG. 6 illustrates a cross-plot of measured and synthetic responses within a section of an EM data log.

FIG. 6 illustrates a possible cross-plot 600 of measured and synthetic responses within a section of an EM data log. The EM data log may span a few or several casing joints (or casing sections). The measured response is acquired with a tool that has a magnetic core (e.g., core 410), and the synthetic response is generated using a computer model that does not include (or account for) such a core. In the plot 600, points 602, 604 and 606 are identified. The points 602, 604, 606 correspond to different points in the EM data log. As illustrated in FIG. 6, the points 602, 604, 606 may be used to produce a linear fit. The linear fit is characterized by a slope of $a_1$ and a y-axis intercept of $a_0$.

The non-linearity in the response could be partially due to the core or non-linearity of the pipes (e.g., effective magnetic permeability of the core decreasing with an increase in the signal level). The non-linearity could also be due to the non-linear interaction between the core and the surrounding ferro-magnetic pipes. Regarding the cross-plot 600, the relationship between the measured and synthetic responses may be described by the Taylor series expansion of Equation (3) below.

$$m = a_0 + a_1 s + a_s s^2 + \ldots \qquad (3)$$

If a nominal operating point is sufficiently outside the non-linear region and the signal level swing across the log is sufficiently small compared to the nominal operating point, then the relationship between the measured and synthetic responses may be well approximated using the first two terms of the Taylor series expansion ($a_0$ and $a_1 s$). Otherwise, using additional higher-order terms may be more advantageous. According to at least one embodiment, an aspect of the calibration process is to determine the coefficients for each channel (e.g., receiver/frequency duplet). According to at least one embodiment, at each point used in the calibration process, underlying properties of the pipes (e.g., diameter, wall thickness, magnetic permeability, electrical conductivity) are determined.

In summary, calibration is performed for any of various reasons. For example, calibration enables using fast (or faster) synthetic models in inversion. In order to detect possible defects in the pipes using receiver voltage measurements, an inversion algorithm is applied to find the optimum thickness and effective permeability of each pipe that minimize the misfit between measurements at each depth and synthetic data generated using a computer model. Radial 1-dimensional (R-1D) models are typically used because these models are much faster than two-dimensional (2-D) models. However, R-1D models cannot account for 2-D features of the tool (e.g., tool 40), such as the presence of a magnetic core inside a transmitter coil and/or a receiver coil. The effect of the presence of the core (on the corresponding magnetic field) can be compensated using calibration constants (e.g., calibration coefficients) computed from the calibration process.

As another example, calibration may be performed to account for discrepancies between the tool (e.g., tool 40) and the synthetic model used in inversion. In addition to the effect of the presence of the core, other systemic mismatches (e.g., any possible phase drifts or flips in measurements, possible drifts in current level) may be compensated through calibration.

As another example, calibration may be performed to estimate an average permeability and a conductivity of the pipes that can be used in further processing. Also, calibration may be performed to improve visualization of raw data. Raw data may involve arbitrary magnitude and phase shifts among different measurements, which can render it difficult for a user to visualize defects purely based on raw data. Calibration may compensate for such shifts and thereby improve visualization.

Various embodiments of this disclosure are directed to a method for calibrating an EM pipe inspection tool while the tool is being run inside the well casings. Calibration coefficients compensate for systematic differences between measured and synthetic responses that may arise from an inadequacy of a synthetic model to describe (or simulate) the physical tool. For example, an R-1D model may be unable to model a magnetic core that is present in the tool. In general, calibration coefficients are a slowly varying function of depth and, therefore, may be assumed to be constant throughout a particular section of a log (e.g., an EM data log). Such a section may span one or more casing joints (or casing sections).

According to at least one embodiment, the calibration coefficients may include multiplicative and additive coefficients. Also according to at least one embodiment, multiple points (two or more points) across the log are jointly inverted to determine calibration coefficients and properties of the pipes at those points. Accordingly, a multi-point calibration is performed. The calibration coefficients are applied to the model that will be used in the inversion of the log. According to at least one embodiment, properties of pipes that are estimated during the calibration process may be used to constrain one or more model parameters while performing the inversion at other log points.

Figure 7:
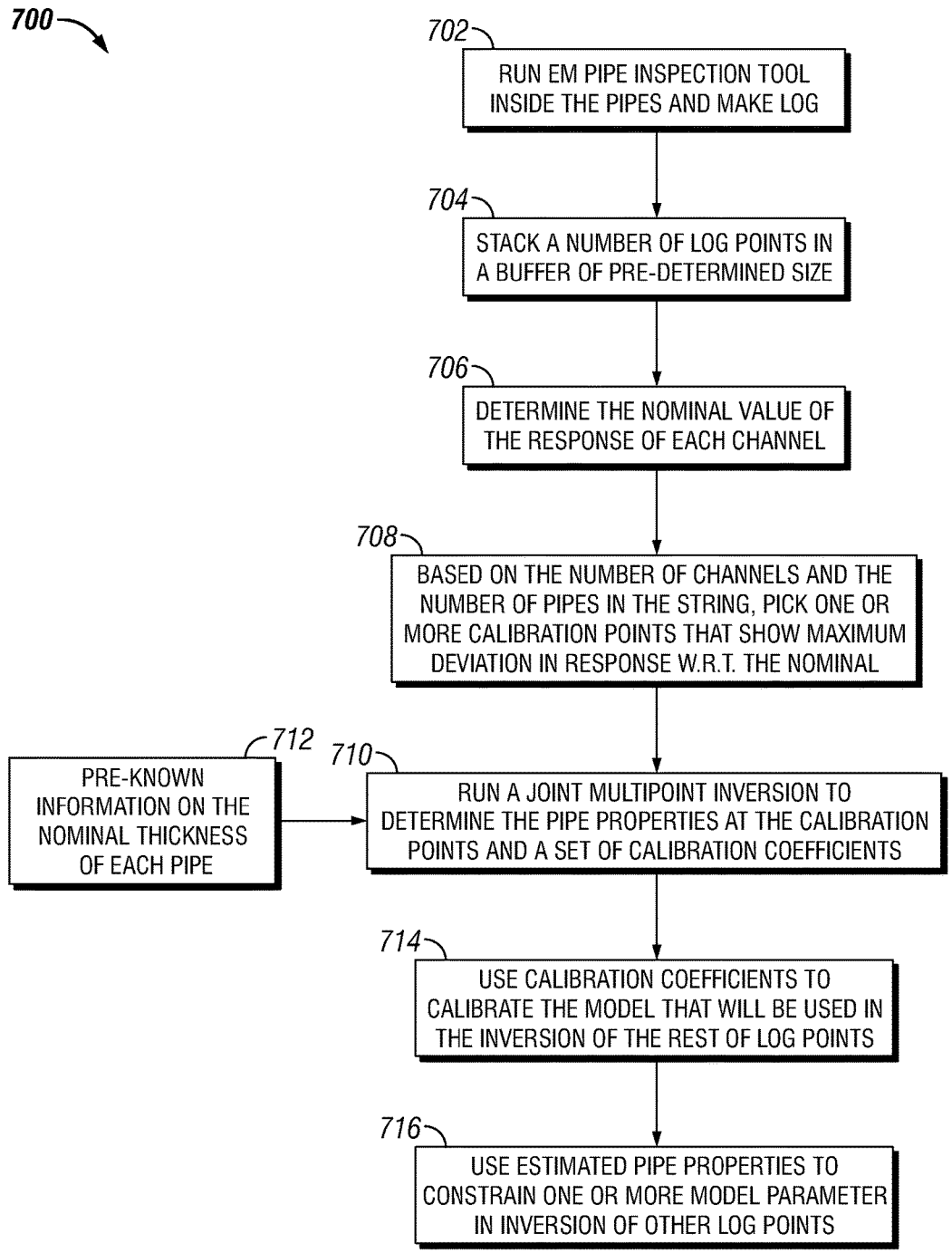
FIG. 7 illustrates a flowchart for calibrating an EM logging tool according to at least one embodiment.

FIG. 7 illustrates a flowchart 700 for calibrating an EM logging tool according to at least one embodiment. As will be described in more detail later, a multi-point calibration is performed. For ease of description, features of the flowchart 700 will be described with reference to a frequency-domain tool that operates at a discrete set of frequencies. However, it is understood that features of the flowchart 700 are also applicable when a time-domain tool is operated.

At block 702, an EM pipe inspection tool (e.g., tool 40) is run inside one or more pipes (e.g., tubing 404, casing 406). Responses are measured by the tool at each of multiple channels. Each channel is defined by a corresponding receiver (e.g., receiver 513, 514, 515, 516, 517 or 518) and a corresponding frequency of the discrete set of frequencies. Responses from the tool are recorded in a log (e.g., EM data log).

At block 704, log points are input to an input data buffer. The input data buffer may be sized such that a buffered log corresponds to one or more casing joints (or casing sections).

At block 706, a nominal value of the response of each channel (e.g., receiver/frequency duplet) is determined. According to at least one embodiment, the nominal value is chosen as the value that occurs (or appears) most often across the log. For example, the nominal value may be determined by computing (or compiling) a histogram for log values and choosing the nominal value to be the value that corresponds to the peak of the histogram. A complex value has a signal magnitude component and a phase component. In this situation, choosing the nominal value may involve computing two histograms (e.g., one for the magnitude and one for the phase of the response of a particular channel) and choosing the values of magnitude and phase that correspond to the peaks of the histograms.

At block 708, one or more calibration points are selected (e.g., in addition to a calibration point that is based on the nominal value of block 706). As will be described in more detail later, the total number of calibration points may be based on the number of channels and the number of pipes in the string. According to at least one embodiment, the one or more calibration points are selected such that the measured responses at the points show (or exhibit) maximum deviation with respect to the nominal value of block 706. If two or more calibration points are selected, then, additionally, the points are selected such that the measured responses at the points show a maximum deviation with respect to each other. The selection will be described in more detail later with reference to an illustrative example.

At block 710, a joint multi-point inversion is run where the nominal response and the measured responses at the selected calibration points (of block 708) are used to solve for the nominal properties of the pipes (e.g., permeability, conductivity), properties of the pipes at each calibration point (thickness, and possibly permeability and conductivity), and/or a set of calibration coefficients that matches the measured responses to the model (e.g., simulated responses). According to at least one embodiment, pre-known information regarding the nominal thicknesses of the pipes (see block 712) is used to constrain the estimated thicknesses of the pipes at a calibration point that corresponds to the nominal value of block 706. The use of such information is referred to as "anchoring."

At block 714, the computed calibration coefficients are used to scale the model that will be used for point-wise inversion of other log points (e.g., points corresponding to further log depths). Estimates of the magnetic permeability and electrical conductivity of the pipes may be a by-product of the calibration process (see, e.g., block 710). At block 716, such estimates are used to constrain estimated parameters during the point-wise inversion of the other log points.

The joint multi-point inversion of block 710 will now be described in more detail with respect to at least one embodiment. Performing such an inversion may involve using a cost function. According to at least one embodiment, the cost function for an N-point joint inversion can be expressed as Equation (4) below.

$$f(a_0, a_1, a_2, \ldots, \mu_1, \ldots, \mu_N, \sigma_1, \ldots, \sigma_N, T_1, \ldots, T_N, D_1, \ldots, D_N) = \sum_{n=1}^{N} \left\| W_{m,abs} \times \left[ abs \left\{ \frac{a_0 + a_1 \times s(\mu_n, \sigma_n, T_n, D_n) + a_2 \times s^2(\mu_n, \sigma_n, T_n, D_n) + \ldots}{m_n} \right\} - 1 \right] \right\|_2^2 + \left\| W_{m,angle} \times \text{angle} \left\{ \frac{a_0 + a_1 \times s(\mu_n, \sigma_n, T_n, D_n) + a_2 \times s^2(\mu_n, \sigma_n, T_n, D_n) + \ldots}{m_n} \right\} \right\|_2^2 \quad (4)$$

In the above Equation (4), variables denote particular values, as follows:

$m_n$: vector of $N_{Rx} \times N_f$ complex measurements at different frequencies and receivers at the $n^{th}$ calibration point. $N_{Rx}$ denotes the number of receivers, and $N_f$ denotes the number of frequencies.

$T_n$: vector of $N_p$ pipe thicknesses at calibration point n. $N_p$ denotes the number of pipes (e.g., concentric pipes) in which the tool is positioned.

$D_n$: vector of $N_p$ pipe diameters at calibration point n. $N_p$ denotes the number of pipes (e.g., concentric pipes) in which the tool is positioned. The diameters could be inner or outer diameters.

$\mu_n$: vector of $N_p$ pipe permeabilities at calibration point n.
$\sigma_n$: vector of $N_p$ pipe conductivities at calibration point n.
$s(\mu_n, \sigma_n, T_n)$: vector of $N_{Rx} \times N_f$ forward model complex responses for pipes with thicknesses $T_n$, relative permeabilities $\mu_n$ and conductivities $\sigma_n$.

$a_0, a_1, a_2, \ldots$: Complex-valued calibration coefficients.
$W_{m,abs}, W_{m,angle}$: measurement-magnitude and measurement-phase weight matrices used to assign different weights to different measurements based on the relative quality or importance of each measurement.

With continued reference to Equation (4)—for an L-dimensional vector x, $\|x\|_2^2 = \Sigma_{i=1}^{L} |x_i|^2$. In addition, it is noted that a division in { } refers to element-wise division.

The cost function of Equation (4) is equal to the misfit computed as the L2 norm of the weighted difference between observed and predicted data, which, in general, are complex numbers for frequency-domain tools. The calibration coefficients and the properties of the pipes are estimated through a constrained optimization procedure to reduce (e.g., minimize) the misfit between the measurements $m_n$ and the calibrated synthetic response $a_0+a_1 \times s(\mu_n, \sigma_n, T_n, D_n)+a_2 \times s^2(\mu_n, \sigma_n, T_n, D_n)+\ldots$.

According to at least one embodiment, the output of the cost function is analyzed (e.g., compared against a pre-defined threshold) to determine if convergence is reached. As long as the cost function is above the pre-defined threshold and the number of iterations has not reached a pre-defined maximum value, the calibration coefficients and the pipe properties are updated. The updates are performed, perhaps subject to constraints, so as to further reduce the misfit in the following iteration.

Examples of particular constraints that may be employed in block 710 (and other blocks of the flowchart 700) will now be described in more detail with respect to at least one embodiment. Such constraints (or model simplifications) may be applied to more readily achieve a unique solution in the inversion of block 710.

As described earlier with reference to block 712, pre-known information (e.g., information that is known a priori) regarding the nominal thicknesses of the pipes may be used to constrain the estimated thicknesses of the pipes at a calibration point that corresponds to the nominal response. This constraint is referred to as "anchoring."

Often, a nominal operating point is sufficiently outside the non-linear region (e.g., in a plot such as plot 600), and the signal level swing across the log is sufficiently small compared to the nominal operating point. In this case, the use of two coefficients $a_0$ and $a_1$ (see Equation (4)) may be sufficient for calibrating the model.

As another example, the relative permeability of the pipes used in well casings can typically range from 1-120. In strings with a large number of pipes (e.g., four or more pipes), the measured responses might not have enough sensitivity to solve for the individual magnetic permeability of each of the pipes. In this situation, the inversion may be regularized by assigning, at each calibration point, a permeability value that is specific to the innermost pipe and an additional permeability value that is common to all other pipes.

As yet another example, the conductivity of the pipes used in well casings can typically range from $3 \times 10^6$-$6 \times 10^6$ S/m. Pipes that are used in a given well are usually made of the same type of steel, and the conductivity does not vary much along the length of the pipes. Therefore, it may be acceptable to assign one conductivity value to all pipes at all calibration points.

As another example, for values of the coefficient $a_1$, an acceptable range may be $1 < abs(a_1) < \mu_{core}$, where $\mu_{core}$ denotes the permeability of the transmitter core. The permeability of the transmitter core may be obtained through experimental measurements at the surface. For values of the coefficient $a_0$, an acceptable range may be $0 < abs(a_0) < \min_n (abs(m_n))$.

As yet another example, to further regularize the inversion, a real-valued multiplicative regularization factor may be multiplied with the additive calibration coefficient $a_0$. The value of the regularization factor may increase gradually from 0 to 1 as the number of iterations increases.

According to an illustrative example, applying the described constraints reduces the number of unknowns U, as expressed in Equation (5) below.

$$U = \underbrace{1}_{\sigma_{avg}} + \underbrace{2 \times N}_{\mu_n} + \underbrace{N_p \times (N-1)}_{T_n} + \underbrace{4 \times N_{Rx} \times N_f}_{a_0, a_1} \quad (5)$$

The number of measurements M may be calculated based on Equation (6) below.

$$M = 2 \times N_{Rx} \times N_f \times N \quad (6)$$

To arrive at an overdetermined system, the number of measurements should be greater than the number of unknowns (i.e., M>U). Therefore, to arrive at an overdetermined system, the number of calibration points should be consistent with Inequality (7) below.

$$N > \frac{1 - N_p + 4 \times N_{Rx} \times N_f}{-2 - N_p + 2 \times N_{Rx} \times N_f} \quad (7)$$

An illustrative example of a multi-point calibration will now be described, with reference to a tool having the axial arrangement of FIG. 5. As described earlier with reference to FIG. 5, the tool has one transmitter (transmitter 502) and six receivers (receivers 513, 514, 515, 516, 517, 518). The receivers are located at different axial spacings away from the transmitter 502, with respect to a direction of logging. In this illustrated example, the transmitter 502 has a magnetic core with a relative permeability of 70.

In this example, the tool is run inside five concentric pipes. Actual characteristics (true characteristics) of the pipes are presented in Table 1 below. The characteristics include the average conductivity $\sigma_{avg}$, the respective permeability values of the five pipes ($\mu_1$, $\mu_2$, $\mu_3$, $\mu_4$, $\mu_5$) and the respective thickness values of the five pipes ($t_1$, $t_2$, $t_3$, $t_4$, $t_5$).

TABLE 1

|  | | $\sigma_{avg}$ [S/m] | $\mu_1$ | $\mu_{2-5}$ | $t_1$ [in.] | $t_2$ [in.] | $t_3$ [in.] | $t_4$ [in.] | $t_5$ [in.] |
|---|---|---|---|---|---|---|---|---|---|
| Cal. Pt 1 | True | $4 \times 10^6$ | 76 | 76 | 0.217 | 0.324 | 0.545 | 0.514 | 0.435 |
| (anchor) | Estmated | $3.85 \times 10^6$ | 75.33 | 75.33 | 0.217 | 0.324 | 0.545 | 0.514 | 0.435 |
| Cal. Pt 2 | True | $4 \times 10^6$ | 76 | 76 | 0.217 | 0.324 | 0.545 | 0.514 | 0.255 |
|  | Estimated | $3.85 \times 10^6$ | 80.6 | 75.33 | 0.206 | 0.336 | 0.523 | 0.533 | 0.26 |
| Cal. Pt 3 | True | $4 \times 10^6$ | 76 | 76 | 0.217 | 0.324 | 0.545 | 0.514 | 0.255 |
|  | Estimated | $3.85 \times 10^6$ | 74.9 | 75.33 | 0.218 | 0.318 | 0.548 | 0.504 | 0.35 |

The number of calibration points that are needed to achieve an overdetermined system when performing the multi-point calibration can be determined using Inequality (7).

In this illustrative example, measurements of the tool are performed at four different frequencies ($f_1$, $f_2$, $f_3$ and $f_4$).

Therefore, the number of frequencies $N_f$=4. Further, the number of pipes $N_p$=5, and the number of receivers $N_{Rx}$=6. Based on Inequality (7), N>2.24. Therefore, at least 3 calibration points are needed.

Accordingly, TABLE 1 lists the characteristics of the pipes at each of 3 calibration points. As will be explained in more detail below, estimates of the characteristics are determined based on measurements at a particular receiver/frequency duplet.

Figure 8:
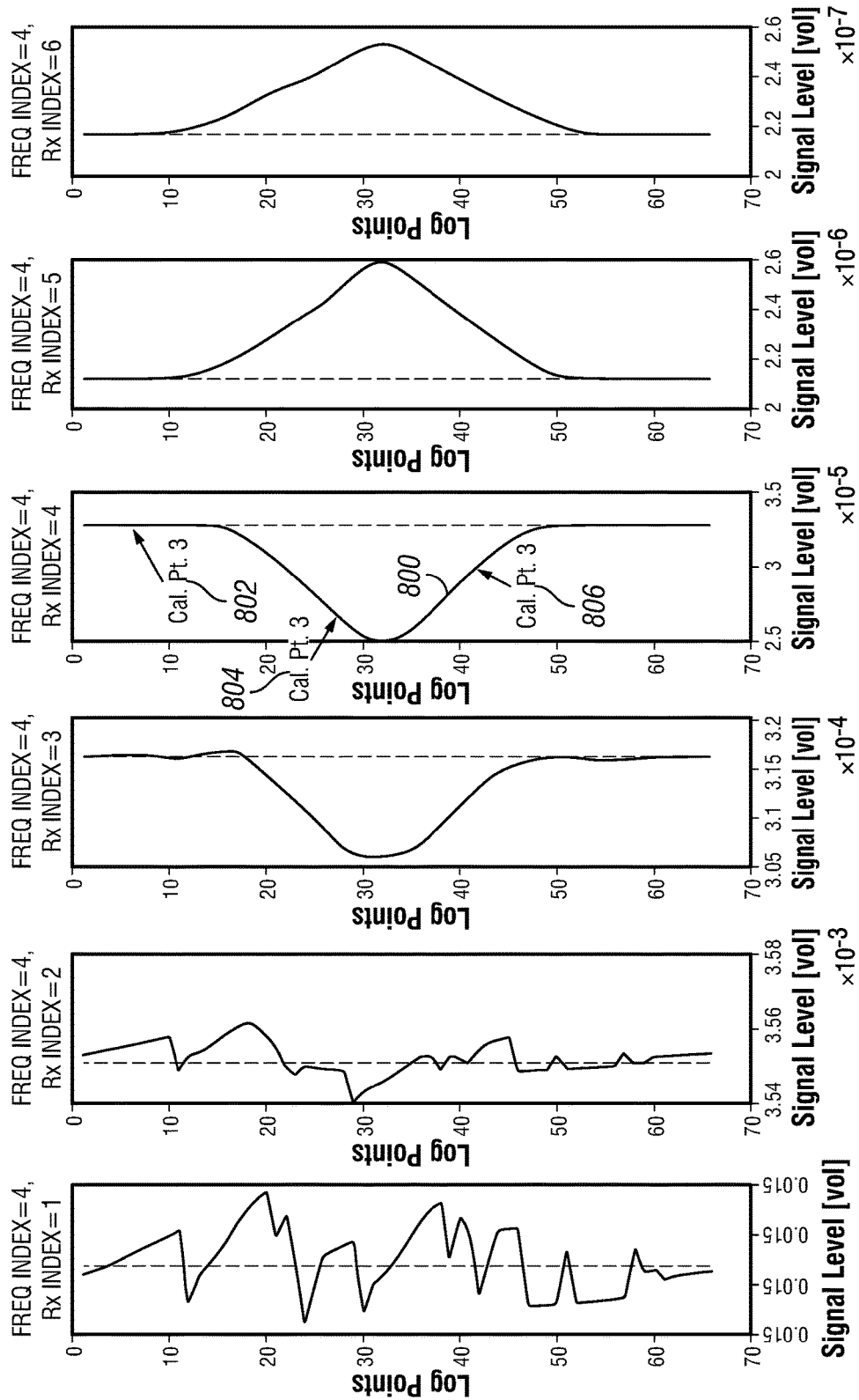
FIGS. 8A to 8F illustrate examples of logs of data measured by the receivers.

FIGS. 8A to 8F illustrate examples of logs of data measured by the receivers. The data are measured at frequency $f_4$. In more detail, FIG. 8A is a log of data measured by a first receiver (e.g., receiver 513). FIG. 8B is a log of data measured by a second receiver (e.g., receiver 514). FIG. 8C is a log of data measured by a third receiver (e.g., receiver 515). FIG. 8D is a log of data measured by a fourth receiver (e.g., receiver 516). FIG. 8E is a log of data measured by a fifth receiver (e.g., receiver 517). FIG. 8F is a log of data measured by a sixth receiver (e.g., receiver 518.)

As described earlier with reference to block 706, a nominal response of a channel is determined. Such a determination will now be described, by way of example, with reference to FIG. 8D.

With reference to FIG. 8D, a plot 800 is of the measurements measured at a channel defined by the fourth receiver and the frequency $f_4$. A first calibration point 802 corresponds to the nominal response of the channel. The calibration point 802 does not necessarily correspond to a specific point in the log (e.g., the plot 800). Rather, the calibration point 802 corresponds to the signal level that is recorded most often in the channel. As such, the calibration point 802 corresponds to multiple points in the log. As described earlier with reference to block 706, a histogram of the recorded signal values may be compiled. In this situation, the calibration point 802 corresponds to the peak of the histogram.

As described earlier with reference to block 708, one or more additional calibration points are selected. Such a selection will now be described in more detail with reference to FIG. 8D.

In the plot 800, a second calibration point 804 and a third calibration point 806 are also identified. The second calibration point 804 is selected based on a correspondence between this point and the point of the plot 800 that has the maximum signal deflection (e.g., maximum signal deviation) relative to the nominal response of the first calibration point 802. As illustrated in FIG. 8B, the difference between the nominal response and the measured responses of the plot 800 is largest at the second calibration point 804.

Once the second calibration point 804 has been selected, the third calibration point 806 is selected. The third calibration point 806 is selected based on a correspondence between this point and the point of the plot 800 that has the maximum signal deflections (e.g., maximum signal deviations) relative to both the nominal response and the measured response at the second calibration point 804. As illustrated in FIG. 8D, the difference between the nominal response and the measured responses of the plot 800 and the difference between the measured response at the second calibration point and the measured responses of the plot 800 are largest at the third calibration point 804.

For choosing the calibration points, the channel of FIG. 8D is used (e.g., instead of the channels of FIG. 8A, FIG. 8B, FIG. 8C, etc.) because this particular channel is defined by a lowest frequency and a receiver coil having a shortest length (e.g., axial length), from among channels at which a maximal deviation with respect to the nominal value is greater than the particular threshold. For example, the value of the threshold may be equal to 10% of the nominal value. As another example, the value of the threshold may be equal to 20% of the nominal value.

Based on the calibration points 802, 804 and 806, a joint multi-point inversion is performed. The inversion may be performed using, for example, the cost function of Equation (4). Calibration coefficients that are determined as a result of performing the multi-point inversion may be used to scale the model that will be used for point-wise inversion of other log points. Estimated values of characteristics of the pipes at each of the three calibration points are also presented in TABLE 1.

According to various embodiments, a multi-point calibration is performed to calibrate an EM logging tool. Methods employing single-point calibrations may also be effective. Single-point calibrations use only multiplicative calibration coefficients to match measured responses to synthetic response. Single-point calibrations may be suitable in the context of casing sections which exhibit relatively small deviations between measured responses and the nominal operating point. However, single-point calibration may become less suitable as deviations with respect to the nominal operating point increase (e.g., due to possible non-linearity in the measured versus synthetic relationship).

It is understood that features of the flowchart 700 are also applicable when using a time-domain tool. For time-domain tools, responses are real-valued. A calibration process similar to the process described earlier with reference to FIG. 7 may be used. For example, with respect to the cost function of Equation (4), only the real components of the responses will contribute to the cost function.

Figure 9:
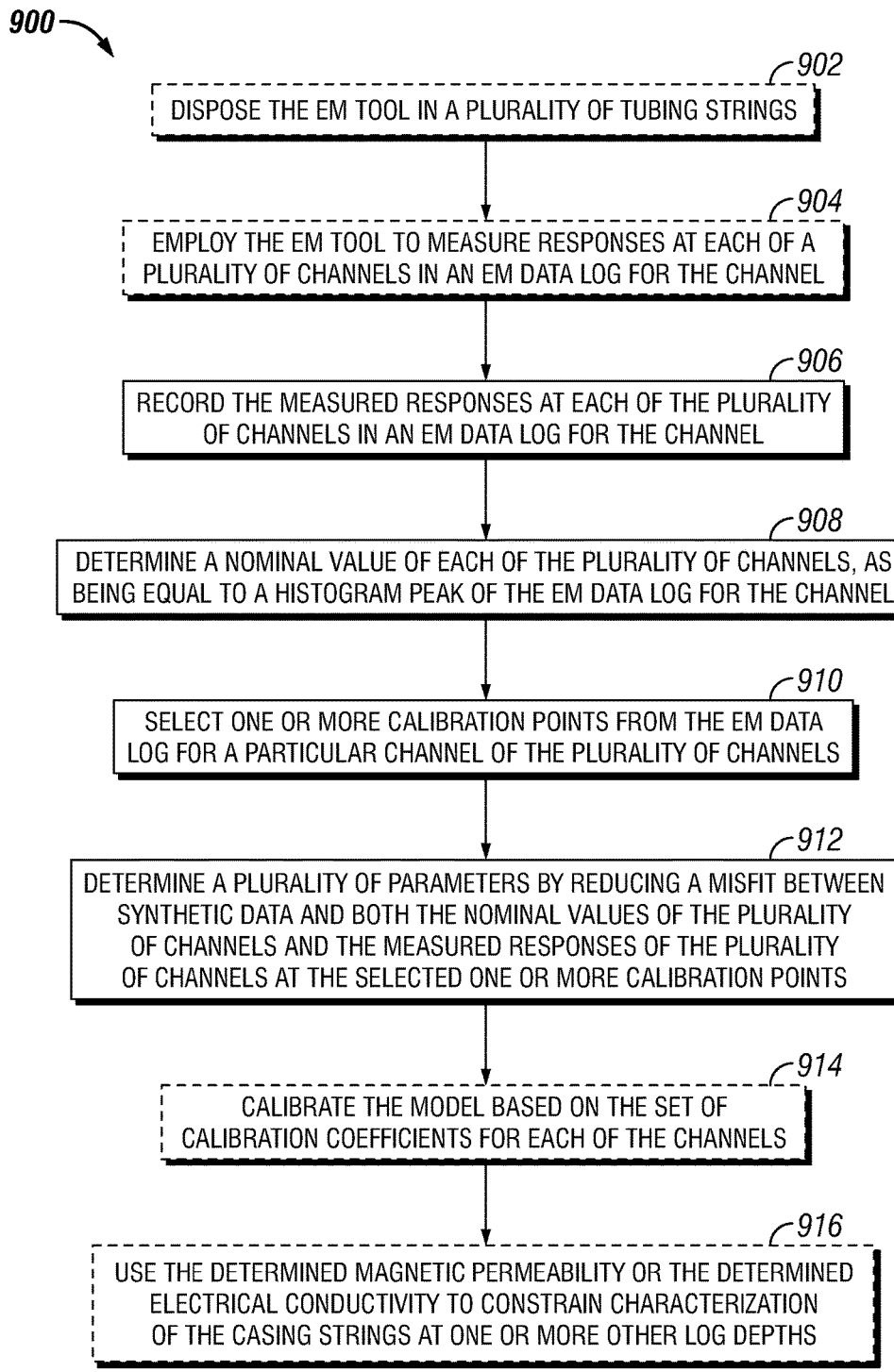
FIG. 9 shows a flowchart of an illustrative method for calibrating an EM logging tool in a multi-string environment.

FIG. 9 shows a flowchart of an illustrative method 900 for calibrating an EM logging tool in a multi-string environment. At block 902, the EM tool (e.g., tool 40) is disposed in a plurality of tubing strings (e.g., inner string, outer string of FIG. 3).

At block 904, the EM tool is employed to measure responses at each of a plurality of channels. Each of the channels is defined by a corresponding receiver coil (e.g., receiver 513, 514, 515, 516, 517, or 518) and a corresponding frequency (e.g., $f_4$ in the example of FIGS. 8A to 8F). At block 906, the measured responses at each of the plurality of channels are recorded in an EM data log for the channel.

At block 906, a nominal value of each of the plurality of channels is determined. The nominal value may be determined as being equal to a histogram peak of the EM data log for the channel. For example, with reference back to FIG. 8D, the nominal value is determined to be the signal level that is recorded most often in the channel (see calibration point 802).

At block 908, one or more calibration points from the EM data log for a particular channel are selected. The calibration points are selected based on a difference between the nominal value of the particular channel and the measured response at the calibration point being greater than a particular threshold. For example, with reference back to FIG. 8D, calibration points 804 and 806 are selected.

At block 910, a plurality of parameters are determined by reducing a misfit between synthetic data, and both the nominal values of the plurality of channels and the measured responses of the plurality of channels at the selected one or more calibration points. In this regard, the plurality of parameters may include a nominal magnetic permeability of each of the tubing strings, a nominal electrical conductivity of each of the tubing strings, a diameter of each of the tubing strings at each of the selected one or more calibration points, a thickness of each of the tubing strings at each of the selected one or more calibration points, a magnetic permeability of each of the tubing strings at each of the selected one or more calibration points, an electrical conductivity of each of the tubing strings at each of the selected one or more calibration points, and/or a set of calibration coefficients for each of the channels. In this regard, a multi-point inversion may be performed.

At block 914, a model that is used to produce the synthetic data is calibrated based on the set of calibration coefficients for each of the channels.

At block 916, the determined magnetic permeability and/or the determined electrical conductivity are used to constrain characterization of the tubing strings at one or more other log depths. For example, the noted parameters are used to constrain an estimation of parameters of the pipes when performing point-wise inversion at the other log depths.

Embodiments disclosed herein include:

A: A calibration system that includes a processor. The processor employs the EM tool to measure responses at each of a plurality of channels. Each of the channels is defined by a corresponding receiver coil of the plurality of receiver coils and a corresponding frequency of a plurality of frequencies. The processor records the measured responses at each of the plurality of channels in an EM data log for the channel. The processor determines a nominal value of each of the plurality of channels, as being equal to a histogram peak of the EM data log for the channel. The processor selects one or more calibration points from the EM data log for a particular channel of the plurality of channels, based on a difference between the nominal value of the particular channel and the measured response at the calibration point being greater than a particular threshold. The processor determines a plurality of parameters by reducing a misfit between synthetic data and both the nominal values of the plurality of channels and the measured responses of the plurality of channels at the selected one or more calibration points. The plurality of parameters includes at least a nominal magnetic permeability of each of the tubing strings, a nominal electrical conductivity of each of the tubing strings, a diameter of each of the tubing strings at each of the selected one or more calibration points, a thickness of each of the tubing strings at each of the selected one or more calibration points, a magnetic permeability of each of the tubing strings at each of the selected one or more calibration points, an electrical conductivity of each of the tubing strings at each of the selected one or more calibration points, or a set of calibration coefficients for each of the channels. The set of calibration coefficients for each of the channels includes an additive coefficient and at least one multiplicative coefficient.

B: A calibration method that includes disposing the EM tool in a plurality of tubing strings, and employing the EM tool to measure responses at each of a plurality of channels, wherein each of the channels is defined by a corresponding receiver coil of the plurality of receiver coils and a corresponding frequency of a plurality of frequencies. The method further includes recording the measured responses at each of the plurality of channels in an EM data log for the channel, and determining a nominal value of each of the plurality of channels, as being equal to a histogram peak of the EM data log for the channel. The method further includes selecting one or more calibration points from the EM data log for a particular channel of the plurality of channels, based on a difference between the nominal value of the particular channel and the measured response at the calibration point being greater than a particular threshold. The method further includes determining a plurality of parameters by reducing a misfit between synthetic data and both the nominal values of the plurality of channels and the measured responses of the plurality of channels at the selected one or more calibration points. The plurality of parameters includes at least a nominal magnetic permeability of each of the tubing strings, a nominal electrical conductivity of each of the tubing strings, a diameter of each of the tubing strings at each of the selected one or more calibration points, a thickness of each of the tubing strings at each of the selected one or more calibration points, a magnetic permeability of each of the tubing strings at each of the selected one or more calibration points, an electrical conductivity of each of the tubing strings at each of the selected one or more calibration points, or a set of calibration coefficients for each of the channels. The set of calibration coefficients for each of the channels includes an additive coefficient and at least one multiplicative coefficient.

Each of the embodiments, A and B, may have one or more of the following additional elements in any combination. Element 1: wherein a difference between the nominal value of the particular channel and the measured response at the particular channel is largest at the selected one or more calibration points. Element 2: wherein: the selected one or more calibration points includes a first calibration point and a second calibration point; and a difference between the nominal value of the particular channel and the measured response at the particular channel is largest at the first calibration point. Element 3: wherein: a difference between the nominal value of the particular channel and the measured response at the particular channel and a difference between the measured response at the first calibration point and the measured response at the particular channel are largest at the second calibrati on point. Element 4: wherein the particular channel is defined by a lowest frequency and a receiver coil having a shortest length, from among channels at which a maximum deviation with respect to the nominal value is greater than the particular threshold. Element 5: wherein: the synthetic data is produced by a model; the plurality of parameters includes the set of calibration coefficients for each of the channels; and the processor further calibrates the model based on the set of calibration coefficients for each of the channels. Element 6: wherein the set of calibration coefficients for each of the channels is used to calibrate the model across one or more sections of the plurality of tubing strings. Element 7: wherein: the plurality of parameters includes at least the magnetic permeability of the tubing strings at each of the selected one or more calibration points, or the electrical conductivity of each of the tubing strings at each of the selected one or more calibration points, and the processor further uses the determined magnetic permeability or the determined electrical conductivity to constrain characterization of the tubing strings at one or more other log depths. Element 8: wherein the plurality of parameters is determined by further using known information regarding the diameter and the thickness of each of the tubing strings. Element 9: wherein the processor determines the plurality of parameters by performing a multi-point inversion.

Element 10: wherein a difference between the nominal value of the particular channel and the measured response at the particular channel is largest at the selected one or more calibration points. Element 11: wherein: the selected one or more calibration points includes a first calibration point and a second calibration point; and a difference between the nominal value of the particular channel and the measured response at the particular channel is largest at the first calibration point. Element 12: wherein: a difference between the nominal value of the particular channel and the measured response at the particular channel and a difference between the measured response at the first calibration point and the measured response at the particular channel are largest at the second calibration point. Element 13: wherein the particular channel is defined by a lowest frequency and a receiver coil having a shortest length, from among channels at which a maximum deviation with respect to the nominal value is greater than the particular threshold. Element 14: wherein: the synthetic data is produced by a model; the plurality of parameters includes the set of calibration coefficients for each of the channels; and the method further includes calibrating the model based on the set of calibration coefficients for each of the channels. Element 15: wherein the set of calibration coefficients for each of the channels is used to calibrate the model across one or more sections of the plurality of tubing strings. Element 16: wherein: the plurality of parameters includes at least the magnetic permeability of the tubing strings at each of the selected one or more calibration points, or the electrical conductivity of each of the tubing strings at each of the selected one or more calibration points, and the method further includes using the determined magnetic permeability or the determined electrical conductivity to constrain characterization of the tubing strings at one or more other log depths. Element 17: wherein the plurality of parameters is determined by further using known information regarding the diameter and the thickness of each of the tubing strings. Element 18: wherein determining the plurality of parameters includes performing a multi-point inversion.

Numerous other variations and modifications will become apparent to those skilled in the art once the above disclosure is fully appreciated. For example, in some embodiments, the order of the processing operations described herein may vary and/or be performed in parallel. It is intended that the following claims be interpreted to embrace all such variations and modifications where applicable.

What is claimed:

1. A method for calibrating an electromagnetic (EM) tool including at least one transmitter coil and a plurality of receiver coils, each of the receiver coils located at a respective axial spacing from the transmitter coil, the method comprising:
    disposing the EM tool in a plurality of tubing strings;
    employing the EM tool to measure responses at each of a plurality of channels, wherein each of the channels is defined by a corresponding receiver coil of the plurality of receiver coils and a corresponding frequency of a plurality of frequencies;
    recording the measured responses at each of the plurality of channels in an EM data log for the channel;
    determining a nominal value of each of the plurality of channels, as being equal to a histogram peak of the EM data log for the channel;
    selecting one or more calibration points from the EM data log for a first channel selected from the plurality of channels, based on a difference between the nominal value of the first channel and the measured response at the calibration point being greater than a threshold;
    determining a plurality of parameters by reducing a misfit between synthetic data and both the nominal values of the plurality of channels and the measured responses of the plurality of channels at the selected one or more calibration points,
    wherein the plurality of parameters comprises at least:
        a nominal magnetic permeability of each of the tubing strings;
        a nominal electrical conductivity of each of the tubing strings;
        a diameter of each of the tubing strings at each of the selected one or more calibration points;
        a thickness of each of the tubing strings at each of the selected one or more calibration points;
        a magnetic permeability of each of the tubing strings at each of the selected one or more calibration points;
        an electrical conductivity of each of the tubing strings at each of the selected one or more calibration points; or
        a set of calibration coefficients for each of the channels.

2. The method of claim 1, wherein a difference between the nominal value of the first channel and the measured response at the particular channel is largest at the selected one or more calibration points.

3. The method of claim 1, wherein: the selected one or more calibration points comprises a first calibration point and a second calibration point; and a difference between the nominal value of the particular channel and the measured response at the particular channel is largest at the first calibration point.

4. The method of claim 3, wherein: a difference between the nominal value of the first channel and the measured response at the particular channel and a difference between the measured response at the first calibration point and the measured response at the particular channel are largest at the second calibration point.

5. The method of claim 1, wherein the first channel is defined by a lowest frequency and a receiver coil having a shortest length, from among channels at which a maximum deviation with respect to the nominal value is greater than the particular threshold.

6. The method of claim 1, wherein: the synthetic data is produced by a model; the plurality of parameters comprises the set of calibration coefficients for each of the channels; and the method further comprises calibrating the model based on the set of calibration coefficients for each of the channels.

7. The method of claim 6, wherein the set of calibration coefficients for each of the channels is used to calibrate the model across one or more sections of the plurality of tubing strings.

8. The method of claim 1, wherein: the plurality of parameters comprises at least the magnetic permeability of the tubing strings at each of the selected one or more calibration points, or the electrical conductivity of each of the tubing strings at each of the selected one or more calibration points, and the method further comprises using the determined magnetic permeability or the determined electrical conductivity to constrain characterization of the tubing strings at one or more other log depths.

9. The method of claim 1, wherein the plurality of parameters is determined by further using known information regarding the thickness and the diameter of each of the tubing strings.

10. The method of claim 1, wherein determining the plurality of parameters comprises performing a multi-point inversion.

11. A calibration system for an electromagnetic (EM) tool including at least one transmitter coil and a plurality of receiver coils, each of the receiver coils located at a respective axial spacing from the transmitter coil, the calibration system comprising:
  a processor that:
    employs the EM tool to measure responses at each of a plurality of channels, wherein each of the channels is defined by a corresponding receiver coil of the plurality of receiver coils and a corresponding frequency of a plurality of frequencies;
    records the measured responses at each of the plurality of channels in an EM data log for the channel;
    determines a nominal value of each of the plurality of channels, as being equal to a histogram peak of the EM data log for the channel;
    selects one or more calibration points from the EM data log for a first channel from the plurality of channels, based on a difference between the nominal value of the first channel and the measured response at the calibration point being greater than a threshold;
    determines a plurality of parameters by reducing a misfit between synthetic data and both the nominal values of the plurality of channels and the measured responses of the plurality of channels at the selected one or more calibration points,
      wherein the plurality of parameters comprises at least:
        a nominal magnetic permeability of each of the tubing strings;
        a nominal electrical conductivity of each of the tubing strings;
        a diameter of each of the tubing strings at each of the selected one or more calibration points;
        a thickness of each of the tubing strings at each of the selected one or more calibration points;
        a magnetic permeability of each of the tubing strings at each of the selected one or more calibration points;
        an electrical conductivity of each of the tubing strings at each of the selected one or more calibration points; or
        a set of calibration coefficients for each of the channels.

12. The calibration system of claim 11, wherein a difference between the nominal value of the first channel and the measured response at the particular channel is largest at the selected one or more calibration points.

13. The calibration system of claim 11, wherein: the selected one or more calibration points comprises a first calibration point and a second calibration point; and a difference between the nominal value of the first channel and the measured response at the particular channel is largest at the first calibration point.

14. The calibration system of claim 13, wherein: a difference between the nominal value of the first channel and the measured response at the particular channel and a difference between the measured response at the first calibration point and the measured response at the particular channel are largest at the second calibration point.

15. The calibration system of claim 11, wherein the first channel is defined by a lowest frequency and a receiver coil having a shortest length, from among channels at which a maximum deviation with respect to the nominal value is greater than the threshold.

16. The calibration system of claim 11, wherein: the synthetic data is produced by a model; the plurality of parameters comprises the set of calibration coefficients for each of the channels; and the processor further calibrates the model based on the set of calibration coefficients for each of the channels.

17. The calibration system of claim 16, wherein the set of calibration coefficients for each of the channels is used to calibrate the model across one or more sections of the plurality of tubing strings.

18. The calibration system of claim 11, wherein: the plurality of parameters comprises at least the magnetic permeability of the tubing strings at each of the selected one or more calibration points, or the electrical conductivity of each of the tubing strings at each of the selected one or more calibration points, and the processor further uses the determined magnetic permeability or the determined electrical conductivity to constrain characterization of the tubing strings at one or more other log depths.

19. The calibration system of claim 11, wherein the plurality of parameters is determined by further using known information regarding the diameter and the thickness of each of the tubing strings.

20. The calibration system of claim 11, wherein the processor determines the plurality of parameters by performing a multi-point inversion.

* * * * *